United States Patent [19]

Castella Sola et al.

[11] Patent Number: 5,243,110

[45] Date of Patent: Sep. 7, 1993

[54] DEHYDROCHLORINATION OF 1,1-BIS(R-PHENYL)-2,2,2-TRICHLOROETHANES

[75] Inventors: Jaume Castella Sola; Jaime Palencia Adrubau, both of Barcelona, Spain

[73] Assignee: Elf Atochem S.A., Puteaux, France

[21] Appl. No.: 901,072

[22] Filed: Jun. 19, 1992

[30] Foreign Application Priority Data

Jun. 19, 1991 [FR] France ............................ 91 07522

[51] Int. Cl.$^5$ .................... C07C 25/20; C07C 17/24
[52] U.S. Cl. ................................ 570/204; 570/205
[58] Field of Search .............................. 570/204, 205

[56] References Cited

U.S. PATENT DOCUMENTS 4,337,368  6/1982  Pytlewski et al. ................ 570/204
4,960,962 10/1990  Brackenridge .................... 570/204

FOREIGN PATENT DOCUMENTS 0584119 10/1959 Canada ............................ 570/204

Primary Examiner—Werren B. Lone
Attorney, Agent, or Firm—Burns, Doane, Swecker & Mathis

[57] ABSTRACT

1,1-Bis(R-phenyl)-2,2,2-trichloroethanes are dehydrochlorinated in high yields, e.g., into 1,1-bis(chlorophenyl)-2,2-dichloroethylenes, by reacting same with an aqueous solution of an alkali metal hydroxide, in liquid state in the presence of a phase transfer agent, e.g., a quaternary ammonium compound, but in the absence of any reaction solvent.

8 Claims, No Drawings

DEHYDROCHLORINATION OF 1,1-BIS(R-PHENYL)-2,2,2-TRICHLOROETHANES

BACKGROUND OF THE INVENTION

1. Field of the Invention

The present invention relates to an improved process for dehydrochlorinating 1,1-bis(R-phenyl)-2,2,2-trichloroethanes.

2. Description of the Prior Art

The 1,1-bis(R-phenyl)-2,2,2-trichloroethanes are known to this art. For example, 1,1-bis(chlorophenyl)-2,2,2-trichloroethane (DDT) is an intermediate compound in the synthesis of 1,1-bis(chlorophenyl)-2,2,2-trichloroethanol, commonly known as dicofol, an acaricide applied to cotton crops and fruit trees.

DDT is dehydrochlorinated to 1,1-bis(chlorophenyl)-2,2-dichloroethylene (DDE) which is then chlorinated to prepare 1,1-bis(chlorophenyl)-1,2,2,2-tetrachloroethane (chloroDDT), which in turn is hydrolyzed to dicofol according to the reaction sequence:

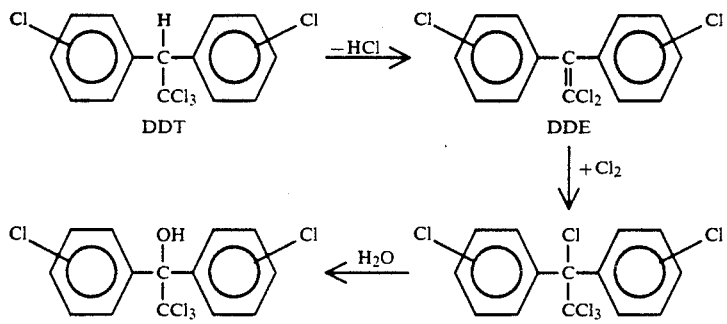

Polish Patent PL-110,642 (*Chemical Abstracts*, Vol. 96: 122386 h (1982)) describes the dehydrochlorination of diphenyltrichloroethane $(C_6H_5)_2CH$—$CCl_3$ to diphenyldichloroethylene $(C_6H_5)_2C$=$CCl_2$, the process being carried out in benzene with sodium hydroxide and methylbis(polyoxyethylene)stearylammonium chloride.

Russian Patent SU-899,524 (*Chemical Abstracts*, Vol. 97: 55461 j (1982)) describes the dehydrochlorination of 1,1-bis(p-chlorophenyl)-2,2,2-trichloroethane (p—$ClC_6H_4)_2CH$—$CCl_3$ with an alkali metal hydroxide, the process being carried out in ethanol or isopropanol.

And Polish Patent PL-112,229 (*Chemical Abstracts*, Vol. 96: 162301 h (1982) describes the dehydrochlorination of bis(para-hydroxyphenyl)trichloroethane (4—$HOC_6H_4)_2CH$—$CCl_3$ in methanol in the presence of a basic, quaternary ammonium ion exchange resin.

The presence of a reaction solvent such as benzene, ethanol, isopropanol or methanol presents difficulties in the event that a chlorination is to be carried out downstream of the dehydrochlorination operation, because such a solvent can itself be chlorinated.

If the product obtained via the dehydrochlorination is to be isolated, the presence of solvent makes the separation more complex.

SUMMARY OF THE INVENTION

Accordingly, a major object of the present invention is the provision of an improved process for the dehydrochlorination of 1,1-bis(R-phenyl)-2,2,2-trichloroethanes by means of an aqueous solution of an alkali metal hydroxide, the reaction being carried out in the absence of solvent but in the presence of a phase transfer agent.

DETAILED DESCRIPTION OF THE PREFERRED EMBODIMENTS OF THE INVENTION

More particularly according to the present invention, the radical R is one or more hydrogen or halogen atoms, alkyl radicals, hydroxyl (OH) or $NO_2$ groups or alkoxy radicals. Methyl, ethyl, propyl and isopropyl are exemplary alkyl radicals. Methoxy and ethoxy are exemplary alkoxy radicals. A combination of different substituents may also be present on the same phenyl nucleus, different substituents on each of the phenyl nuclei, only one substituted phenyl nucleus, or any combination of these substituents.

Although the process may be carried out over a wide pressure range, it is conducted at sufficient pressure to maintain the 1,1-bis(R-phenyl)-2,2,2-trichloroethane and the aqueous alkali metal hydroxide solution in the liquid state.

By "phase transfer agent" is intended a reagent which permits contact between the compound to be dehydrochlorinated and the alkali metal hydroxide. Numerous materials are known to this art which perform this function. For example, the quaternary ammonium compounds are representative, e.g., dimethyllaurylbenzylammonium chloride.

It is also within the scope of this invention to incrementally add the alkali metal hydroxide solution a number of times over the course of the reaction, or to supplement the alkali metal hydroxide content of the reaction mixture by additions of anhydrous or highly concentrated alkali metal hydroxide, such as flaked potassium hydroxide or sodium hydroxide. This permits a reduction in the amount of alkali metal hydroxide used, while maintaining the sodium chloride formed in solution. Upon completion of the reaction, it suffices to separate off the organic phase containing the compound to be dehydrochlorinated and the dehydrochlorinated compound from the alkaline aqueous phase; this operation can be carried out simply by phase separation.

In order to further illustrate the present invention and the advantages thereof the following specific examples are given, it being understood that same are intended only as illustrative and in nowise limitative.

EXAMPLE 1 (Comparative)

420 g of 1,1-bis(chlorophenyl)-2,2,2-trichloroethane were melted and 270 g of 50% strength aqueous sodium hydroxide were introduced therein with stirring and at a temperature of 100°–105° C. After 20 hours of reaction, the mixture was diluted with 300 g of water. The organic phase was separated off and washed twice with 100 g of water and 371.9 g of a mixture of 1,1-bis(chlorophenyl)-2,2-dichloroethylene and 1,1-bis(chlorophenyl)-2,2,2-trichloroethane (15.5%) was obtained.

EXAMPLE 2 (Comparative)

60.6 g of 50% strength aqueous sodium hydroxide and two drops of an antifoaming agent were added to a solution of 250 g of 1,1-bis(chlorophenyl)-2,2,2-trichloroethane in 250 g of isobutanol. The mixture was heated until the isobutanol/water azeotrope distilled, while being maintained at reflux for 1 hour. The water was separated off by azeotropic distillation of the water-/isobutanol, while adding isobutanol.

After separation of the water, the separated solid phase was filtered off at room temperature and the isobutanol was distilled from the liquid phase. 217.9 g of 1,1-bis(chlorophenyl)-2,2-dichloroethylene were obtained (y=97.2%) with 0.18% of 1,1-bis(chlorophenyl)-2,2,2-trichloroethane.

EXAMPLE 3 (Comparative)

201.5 g of 28% strength aqueous sodium hydroxide and 2.0 g of dimethyllaurylbenzylammonium chloride were added to a solution of 250 g of 1,1-bis(chlorophenyl)-2,2,2-trichloroethane in 100 g of monochlorobenzene at 50° C. The mixture was heated at reflux (90° C.) for 20 hours. The organic phase was separated by phase separation and was washed three times with 100 g of water. After distillation of the monochlorobenzene, 219.3 g of 1,1-bis(chlorophenyl)-2,2-dichloroethylene were obtained (y=97.8%) with 0.10% of 1,1-bis(chlorophenyl)-2,2,2-trichloroethane.

EXAMPLE 4

150 g of solid 1,1-bis(chlorophenyl)-2,2,2-trichloroethane were added to 248.8 g of a 27.2% strength aqueous sodium hydroxide solution maintained at 93° C. 1.4 g of dimethyllaurylbenzylammonium chloride were added thereto. The temperature increased from 93° to 103° C. The addition of solid 1,1-bis(chlorophenyl)-2,2,2-trichloroethane was continued up to a total amount of 300 g. 1.1 g of dimethyllaurylbenzylammonium chloride were added again and the temperature was maintained between 100° and 105° C. for 14 hours, 30 min. The organic phase was separated off by phase separation and washed three times with 100 g of a 1N solution of sulfuric acid and with water (100 g). 263.7 g of 1,1-bis(chlorophenyl)-2,2-dichloroethylene were obtained (y=98.0%) with 0.09% of 1,1-bis(chlorophenyl)-2,2,2-trichloroethane.

EXAMPLE 5

990 kg of solid 1,1-bis(chlorophenyl)-2,2,2-trichloroethane were charged into the basic aqueous phase emanating from an upstream dehydrochlorination operation. The charging period was 2 hours to avoid the formation of solid masses inside the reactor. 5 kg of dimethylbenzyllaurylammonium chloride were added, while intense stirring was continued for 4 hours at 100°. After 1 hour at rest, the aqueous phase was separated off and 268 kg of 50% strength sodium hydroxide were added and the dehydrochlorination was continued with stirring at 100° C. for 10 hours. After dilution with 560 kg of water and 1 hour at rest, the organic phase was drawn off and the aqueous phase was retained for the following operation. The organic phase was then washed 3 times with 250 kg of a 1N solution of sulfuric acid and 879 kg of 1,1-bis(chlorophenyl)-2,2-dichloroethylene were obtained.

EXAMPLE 6

The procedure of Example 5 was repeated, except that technical 1,1-bis(chlorophenyl)-2,2,2-trichloroethane in the molten state at 92° C. was used at the outset.

The 1,1-bis(chlorophenyl)-2,2,2-trichloroethane in the liquid state was added to the basic aqueous phase from an upstream dehydrochlorination operation and the dehydrochlorination was initiated with the addition of 5 kg of dimethylbenzyllaurylammonium chloride, while intense stirring was maintained for 4 hours at 100° C.

The procedure was then as is Example 5; the same results were obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the dehydrochlorination of a 1,1-bis(R-phenyl)-2,2,2-trichloroethane, comprising reacting 1,1-bis(R-phenyl)-2,2,2-trichloroethane, wherein R is a hydrogen or halogen atom, hydroxyl or nitro group, or alkyl or alkoxy radical, with an aqueous solution of an alkali metal hydroxide in liquid state in the presence of a phase transfer agent, but in the absence of any reaction solvent.

2. The process as defined by claim 1, said phase transfer agent comprising a quaternary ammonium compound.

3. The process as defined by claim 2, said phase transfer agent comprising dimethyllaurylbenzylammonium chloride.

4. The process as defined by claim 1, comprising incrementally adding said alkali metal hydroxide to the liquid medium of reaction.

5. The process as defined by claim 1, said alkali metal hydroxide comprising sodium hydroxide.

6. The process as defined by claim 1, 1,1-bis(R-phenyl)-2,2,2-trichloroethane comprising a 1,1-bis(chlorophenyl)-2,2,2-trichloroethane.

7. A process for the dehydrochlorination of a 1,1-bis(R-phenyl)-2,2,2-trichloroethane, comprising reacting 1,1-bis(R-phenyl)-2,2,2-trichloroethane, wherein R is a hydrogen or halogen atom, hydroxyl or nitro group, or alkyl or alkoxy radical, with an aqueous solution of an alkali metal hydroxide in liquid state in the presence of a phase transfer agent which permits contact between the compound to be dehydrochlorinated and the alkali metal hydroxide, but in the absence of any reaction solvent to obtain a dehydrochlorinated product of said 1,1-bis(R-phenyl)-2,2,2-trichloroethane.

8. A process for the dehydrochlorination of a 1,1-bis(R-phenyl)-2,2,2-trichloroethane, comprising reacting 1,1-bis(R-phenyl)-2,2,2-trichloroethane, wherein R is a hydrogen or halogen atom, hydroxyl or nitro group, or alkyl or alkoxy radical, with an aqueous solution of an alkali metal hydroxide in liquid state in the presence of a phase transfer agent comprising a quaternary ammonium compound which permits contact between the compound to be dehydrochlorinated and the alkali metal hydroxide, but in the absence of any reaction solvent to obtain a dehydrochlorinated product of said 1,1-bis(R-phenyl)-2,2,2-trichloroethane.

* * * * *